United States Patent
Jong et al.

(10) Patent No.: US 7,465,841 B2
(45) Date of Patent: Dec. 16, 2008

(54) METHOD AND DEVICE FOR PURIFYING 1,4-BIS (BROMODIFLUOROMETHYL) BENZENE

(75) Inventors: Shean-Jeng Jong, Longtan Township, Taoyuan County (TW); Chun-Hsu Lin, Longtan Township, Taoyuan County (TW); Chao-Chou Tu, Longtan Township, Taoyuan County (TW); Chung-Chien Chang, Longtan Township, Taoyuan County (TW)

(73) Assignee: Chung Shan Institute of Science and Technology, Taoyuan County (TW)

( * ) Notice: Subject to any disclaimer, the term of this patent is extended or adjusted under 35 U.S.C. 154(b) by 410 days.

(21) Appl. No.: 10/898,925

(22) Filed: Jul. 27, 2004

(65) Prior Publication Data

US 2005/0256349 A1    Nov. 17, 2005

(30) Foreign Application Priority Data

May 11, 2004    (TW) .............................. 93113187 A

(51) Int. Cl.
*C07C 17/00* (2006.01)
*C07C 19/00* (2006.01)
*C07C 21/00* (2006.01)
*C07C 23/00* (2006.01)
*C07C 25/00* (2006.01)

(52) U.S. Cl. ..................................................... 570/101

(58) Field of Classification Search ................ 570/101
See application file for complete search history.

(56) References Cited

U.S. PATENT DOCUMENTS 5,268,202 A    12/1993    You et al.
5,874,608 A *    2/1999    Pfirmann et al. ............... 560/8

FOREIGN PATENT DOCUMENTS

NL    6411094 A *    3/1965
NL    6411094 A *    3/1965

OTHER PUBLICATIONS

Bruns et al (Journal—Association of Official Analytical Chemists, 1980, 63(1), 56-60).*

* cited by examiner

*Primary Examiner*—Daniel M Sullivan
*Assistant Examiner*—Kellette Gale
(74) *Attorney, Agent, or Firm*—Rabin & Berdo, P.C.

(57) ABSTRACT

A method and a device for purifying 1,4-bis(bromodifluoromethyl)benzene are disclosed. In order to solve the problem of hard to purify and separate 1,4-bis(bromodifluoromethyl) benzene crude products, diphenylmethane that has a higher boiling point and does not interact with 1,4-bis(bromodifluoromethyl)benzene is mixed with the 1,4-bis(bromodifluoromethyl)benzene crude products for evaporation. Afterwards, the purity of the vaporized product is detected and only that reaching an expected purity is collected to obtain high-purity 1,4-bis(bromodifluoromethyl)benzene.

9 Claims, 2 Drawing Sheets

METHOD AND DEVICE FOR PURIFYING 1,4-BIS (BROMODIFLUOROMETHYL) BENZENE

BACKGROUND OF THE INVENTION

1. Field of Invention

The invention relates to a purification method and, in particular, to a method for purifying 1,4-bis(bromodifluoromethyl)benzene.

2. Related Art

Low dielectric-constant materials have smaller dielectric constants that can reduce the interference of currents among wires to increase the transmission functions inside integrated circuits (IC). It has become a trend to apply low dielectric-constant materials to various products. The speed of many advanced products can be increased by using low dielectric-constant materials. Products with low interference wires can reduce power consumption and increase the efficiency to dominate the market.

As reported in the U.S. Pat. No. 5,268,202, 1,4-bis(bromodifluoromethyl)benzene is one of the low dielectric-constant materials for IC. The compound can be synthesized from 1,4-bis(difluoromethyl)benzene by bromination. After the reaction, the 1,4-bis(bromodifluoromethyl)benzene crude product contains a little yet-dried solvent, reactant 1,4-bis (difluoromethyl)benzene, (1-bromodifluoromethyl 4-difluoromethyl)benzene, and other side products with higher or lower boiling points. However, these impurities have similar polarities as the main product. Therefore, it is hard to use a silica gel column to purify the 1,4-bis(bromodifluoromethyl) benzene.

SUMMARY OF THE INVENTION

A primary objective of the invention is to provide a method for purifying 1,4-bis (bromodifluoromethyl)benzene.

The disclosed method for purifying 1,4-bis(bromodifluoromethyl)benzene includes the steps of: mixing 1,4-bis(bromodifluoromethyl)benzene crude products with diphenylmethane to obtain a mixture; evaporating the mixture to obtain an evaporated product; detecting the purity of the evaporated products in batches; abandoning the evaporated product if the purity is lower than an expected value, thereby collecting those reaching the expected purity.

According to the above purification method, the invention also provides a device for purifying 1,4-bis(bromodifluoromethyl)benzene. The device is comprised of a flask, a heater, a column, and a collecting cup. The column contains a condenser and a dripping device. The heater provides heat to evaporate the mixture of 1,4-bis(bromodifluoromethyl)benzene and diphenylmethane crude products in the flask. The vapor goes through the column connected to the opening of the flask and condensates in the condenser. The distilled liquid flows out via the dripping device into the collecting cup.

BRIEF DESCRIPTION OF THE DRAWINGS

The invention will become more fully understood from the detailed description given hereinbelow illustration only, and thus are not limitative of the present invention, and wherein.

DETAILED DESCRIPTION OF THE INVENTION

Figure 1:
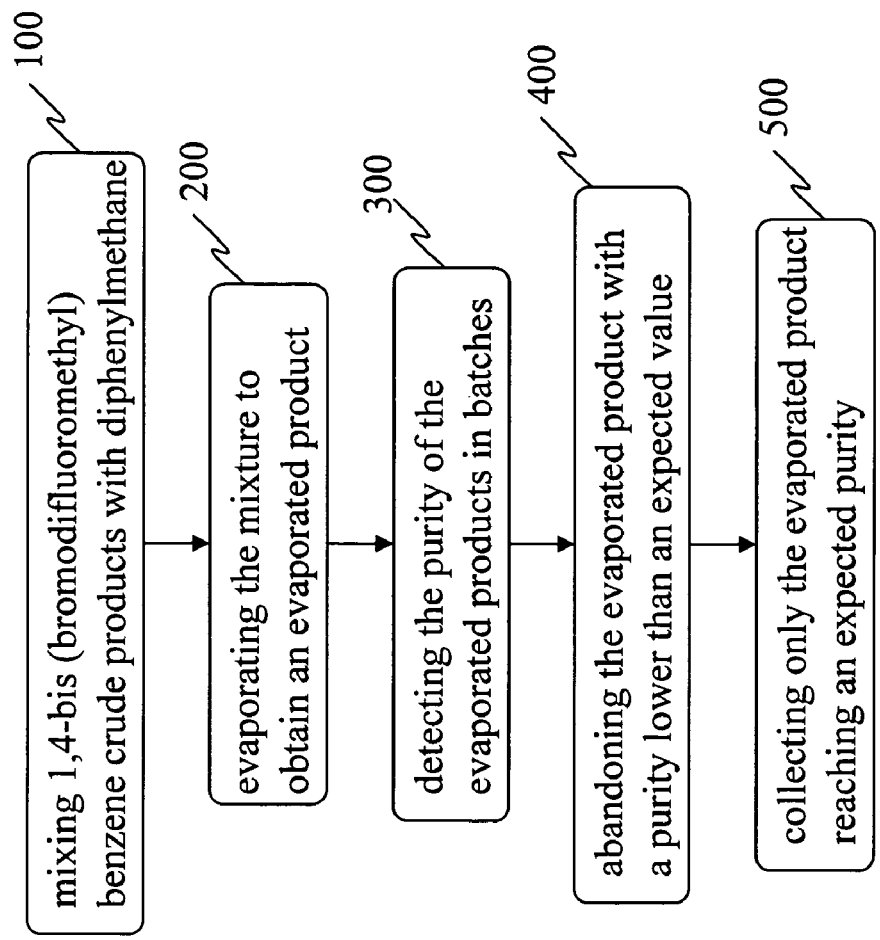
FIG. 1 is a flowchart of the disclosed method for purifying 1,4-bis (bromodifluoromethyl)benzene.

As shown in FIG. 1, the disclosed method for purifying 1,4-bis(bromodifluoromethyl)benzene include the following steps:

First, solutions resulting from addition of high boiling-point solvent to 1,4-bis(bromodifluoromethyl)benzene crude products, wherein diphenylmethane is used as the solvent in one embodiment, are mixed to obtain their mixture (step 100). The mixture is evaporated under ambient pressure or a reduced pressure, 10 torr being utilized in one embodiment, to obtain evaporated products (step 200). A gas chromatography (GC) is used to detect the purity of the evaporated products in batches (step 300). The evaporated product with purity lower than an expected value is abandoned (step 400). Finally, the evaporated product reaching the expected purity is collected (step 500).

Figure 2:
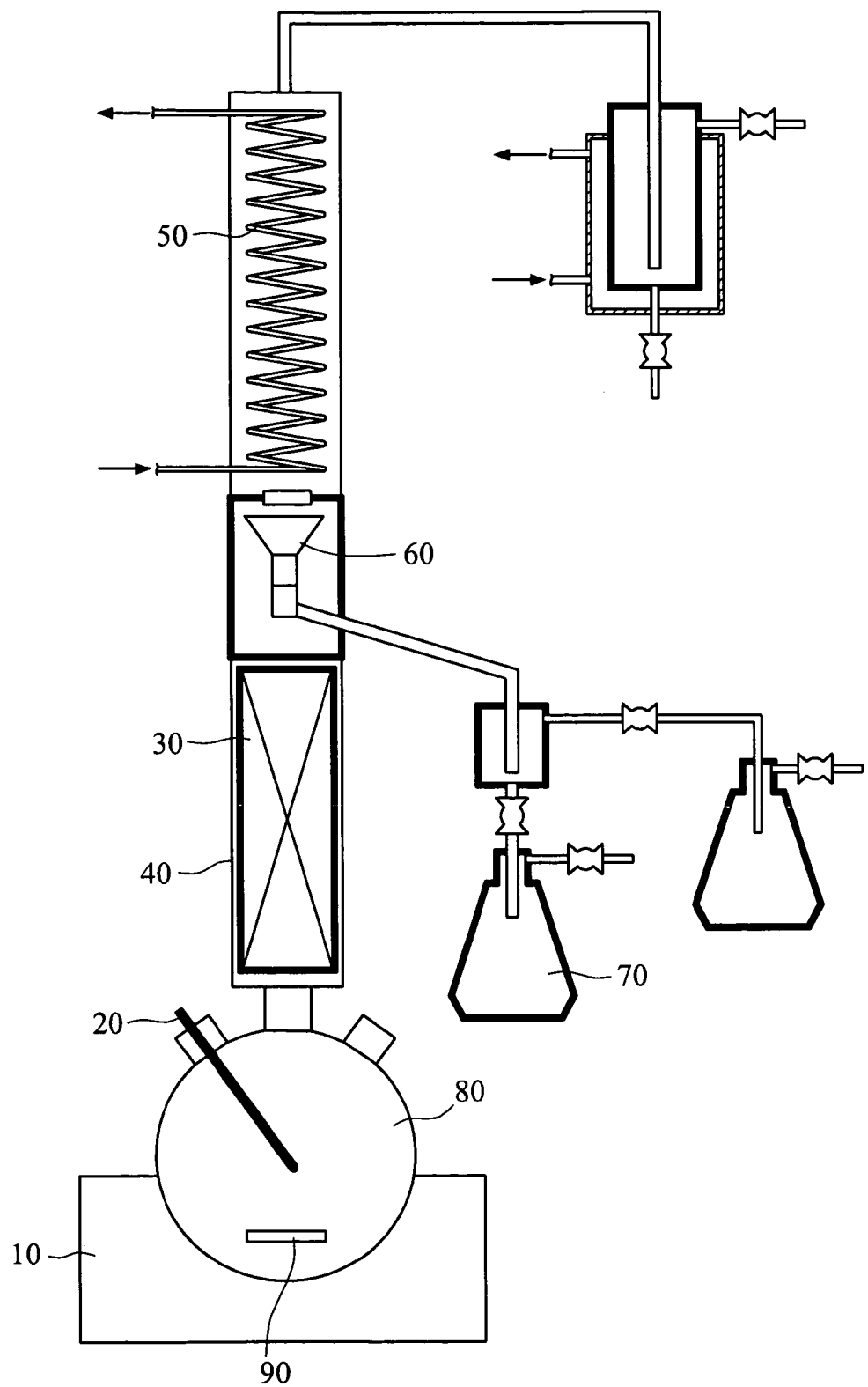
FIG. 2 is a schematic view of the disclosed device for purifying 1,4-bis (bromodifluoromethyl)benzene.

As shown in FIG. 2, the disclosed purification device contains a flask 80, a heater 10, a column 40, a collecting cup 70, a temperature controller 20, and a temperature recorder 30. The flask 80 is a 2-liter round-bottom flask for accommodating the mixture of 1,4-bis(bromodifluoromethyl)benzene crude products and diphenylmethane. It further contains a magnetic stirrer 90 for stirring the mixture. The heater 10 is an electromagnetic heating stirrer. The round-bottom flask 80 is disposed on the heater 10. The magnetic stirrer 90 is driven by the rotating magnet inside the heater 10 in order to obtain a homogeneous mixture. Electric heat is provided to evaporate the mixture into vapor. The column 40, of length 50 cm and diameter 3 cm, is connected to the opening of the flask 80. It is filled with several U-shape ceramic fillings (the ceramic fillings are Rasching ceramics with a diameter of 0.5 cm) as the evaporation plate, which prevents early condensation of the vapor that can result in residues. On the other hand, the column 40 further contains a condenser 50 and a dripping device 60. The circulation temperature in the condenser 50 is −10° C. The vapor condenses into an evaporated liquid by the condenser 50. The evaporated liquid then flows via the dripping device 60 into the collecting cup 70. The temperature controller 20 and the temperature recorder 30 are used to control and record the temperature. The purification device can further include a vacuum pump in order to maintain the pressure under 10 torr.

In the following, we further explain the principles of purifying 1,4-bis (bromodifluoromethyl)benzene. We use an embodiment to verify the principles.

The disclosed method for purifying 1,4-bis(bromodifluoromethyl)benzene is to evaporate the mixture of 1,4-bis(bromodifluoromethyl)benzene crude products and diphenylmethane. The evaporate product is detected using the GC, and the impurities are separated. The reason of adding diphenylmethane is that its boiling point is higher than that of 1,4-bis (bromodifluoromethyl)benzene. It does not evaporate or interact with 1,4-bis(bromodifluoromethyl)benzene during the evaporation process. Therefore, it is left inside the flask 80 and the column 40 after evaporation. 1,4-bis(bromodifluoromethyl)benzene is pushed out to reduce their residues on the flask 80 and the column 40. One is thus able to obtain high-purity 1,4-bis (bromodifluoromethyl)benzene.

In this embodiment, 1-liter 1,4-bis(bromodifluoromethyl) benzene crude products and 420-ml diphenylmethane are mixed in the round-bottom flask 80. The mixture is evaporated under a pressure of 10 torr. The vapor passes through the column 40 filled with U-shape ceramics. After condensation by the condenser 50, the evaporated liquid flows into the collecting cup 70 via the dripping device 60. Whenever 5 gram of the evaporated liquid is collected, it is detected using the GC (whose column model is Cp-Sil 43 CB). The first 140 grams of evaporated liquid with more impurities are directly tossed away. The rest 1,4-bis(bromodifluoromethyl)benzene can reach a purity of above 99.6%, which is the expectation value of the invention. The evaporation process continues until the residual 1,4-bis(bromodifluoromethyl)benzene contents inside the flask 80 is about 1%, as detected by the GC. Totally, 800 grams of 1,4-bis(bromodifluoromethyl)benzene is collected in this embodiment.

In summary, the invention evaporates the mixture of 1,4-bis(bromodifluoromethyl)benzene crude products and diphenylmethane in order to reduce the residues of 1,4-bis(bromodifluoromethyl)benzene and only collects an evaporated liquid reaching an expected purity. This can separate impurities that are hard to remove from a silica gel column.

Certain variations would be apparent to those skilled in the art, which variations are considered within the spirit and scope of the claimed invention.

What is claimed is:

1. A method for purifying 1,4-bis(bromodifluoromethyl)benzene, comprising the steps of:
   mixing diphenylmethane with 1,4-bis(bromodifluoromethyl)benzene crude products to obtain a mixture, the diphenylmethane having a boiling point higher than that of the 1,4-bis(bromodifluoromethyl)benzene crude products;
   evaporating the mixture to obtain an evaporated liquid in a single-stage evaporating process and to provide an evaporated liquid which is purified 1,4-bis(bromodifluoromethyl)benzene;
   detecting the purity of the evaporated liquid in batches; and
   collecting selected batches of the evaporated liquid based on a result of said detecting.

2. The method for purifying 1,4-bis(bromodifluoromethyl)benzene of claim 1, wherein the 1,4-bis(bromodifluoromethyl)benzene crude products are synthesized from 1,4-bis(difluoromethyl)benzene by bromination.

3. The method for purifying 1,4-bis(bromodifluoromethyl)benzene of claim 1, wherein the step of evaporating the mixture is performed under a reduced pressure.

4. The method for purifying 1,4-bis(bromodifluoromethyl)benzene of claim 1, wherein the step of detecting the purity of the evaporate product is performed using gas chromatography (GC).

5. The method for purifying 1,4-bis(bromodifluoromethyl)benzene of claim 3, wherein the reduced pressure is below 10 torr.

6. The method for purifying 1,4-bis(bromodifluoromethyl)benzene of claim 1, wherein the selected batches have a purity exceeding 99.6%.

7. A method for purifying 1,4-bis(bromodifluoromethyl)benzene, comprising the steps of:
   synthesizing 1,4-bis(bromodifluoromethyl)benzene from 1,4-bis(difluoromethyl)benzene by bromination to provide 1,4-bis(bromodifluoromethyl)benzene crude products;
   mixing diphenylmethane with the 1,4-bis(bromodifluoromethyl)benzene crude products to obtain a mixture, the diphenylmethane having a boiling point higher than that of the 1,4-bis(bromodifluoromethyl)benzene crude products;
   evaporating the mixture under a reduced pressure to obtain an evaporated liquid in a single-stage evaporating process and to provide an evaporated liquid which is purified 1,4-bis(bromodifluoromethyl)benzene;
   detecting the purity of the evaporated liquid in batches using gas chromatography (GC); and
   collecting selected batches of the evaporated liquid based on a result of said detecting, and discarding unselected batches of the evaporated liquid.

8. The method for purifying 1,4-bis(bromodifluoromethyl)benzene of claim 7, wherein evaporating the mixture takes place under a reduced pressure which is below 10 torr.

9. The method for purifying 1,4-bis(bromodifluoromethyl)benzene of claim 7, wherein the selected batches have a purity exceeding 99.6%.

* * * * *